United States Patent [19]

Nadelson

[11] 4,035,508

[45] July 12, 1977

[54] BIS-SUBSTITUTED BENZYL METHANAMINES

[75] Inventor: Jeffrey Nadelson, Lake Parsippany, N.J.

[73] Assignee: Sandoz, Inc., E. Hanover, N.J.

[21] Appl. No.: 642,190

[22] Filed: Dec. 18, 1975

[51] Int. Cl.$^2$ .................... A01N 9/20; A01N 9/24; C07C 87/28

[52] U.S. Cl. ............................ 424/316; 260/340.7; 260/469; 260/475 R; 260/501.18; 260/570.8 R; 424/330

[58] Field of Search ............... 260/570.8 R, 501.18, 260/501.19; 424/316, 330

[56] References Cited

U.S. PATENT DOCUMENTS 3,689,504   9/1972   Horrom ...................... 260/570.8 X Primary Examiner—Robert V. Hines
Attorney, Agent, or Firm—Gerald D. Sharkin; Robert S. Honor; Timothy G. Rothwell

[57] ABSTRACT

Bis-substituted benzyl methanamines, e.g. 1-bis(p-pivaloylbenzyl)methanamine are prepared by hydrolyzing a corresponding N-[bis(p-pivaloylbenzyl)methyl]carbamic acid, alkyl ester and are useful as hypolipidemic agents.

6 Claims, No Drawings

BIS-SUBSTITUTED BENZYL METHANAMINES

This invention relates to bis-substituted benzyl methanamines, which exhibit hypolipidemic activity. More particularly, it relates to bis-substituted benzyl methanamines, intermediates and certain pharmaceutically acceptable salts thereof, and to methods for their preparation.

The compounds of this invention may be represented by the following structural formula:

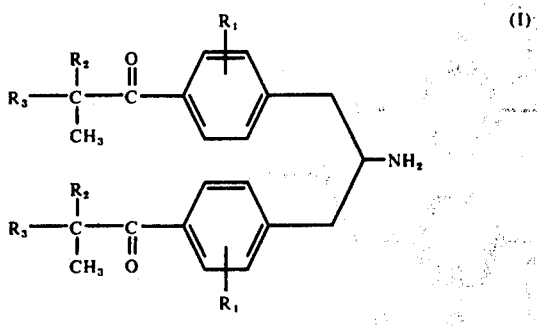

where $R_1$ represents hydrogen or halo having an atomic weight of about 19 to 36, and $R_2$ and $R_3$ each independently represent lower alkyl having 1 to 2 carbon atoms, i.e. methyl or ethyl.

The compounds of formula (I) are prepared according to the following reaction scheme:

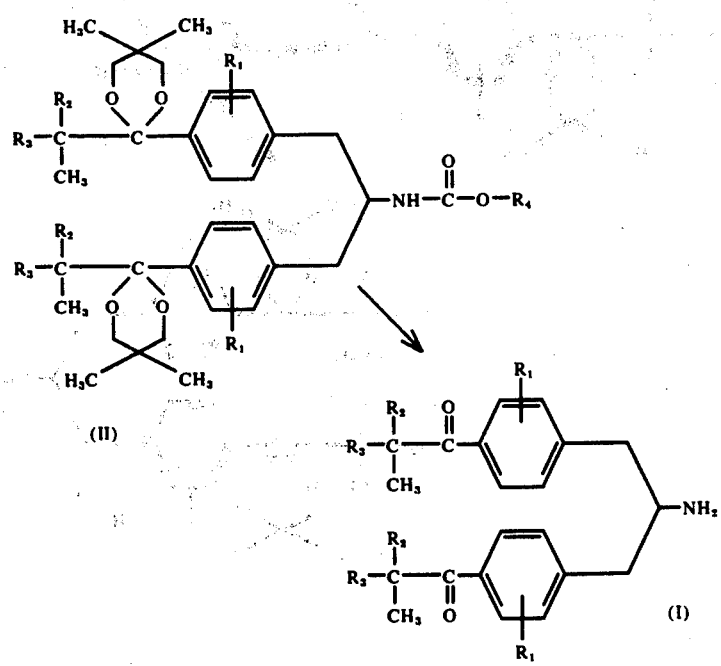

where $R_4$ represents lower alkyl having 1 to 4 carbon atoms, e.g. methyl, ethyl, isopropyl and the like, and $R_1$, $R_2$ and $R_3$ are as defined above.

The compounds of formula (I) are prepared by hydrolyzing a compound of the formula (II) in the presence of an inorganic acid and an aqueous solvent. Although the particular inorganic acid employed is not critical, it is preferred that the reaction be run in the presence of sulfuric acid, phosphoric acid, hydrobromic acid or hydrochloric acid, the latter being especially preferred. The particular aqueous solvent employed is not critical, although it is preferred that the reaction be carried out in the presence of an aqueous solvent such as water or a mixture of water and water-soluble organic solvent, or an excess of the acid utilized above and water, the latter being especially preferred. The temperature of the reaction is not critical, but it is preferred that the reaction be run from about 70° to 150° C., preferably the reflux temperature of the solvent. The reaction is run from about 2 to 10 hours, preferably from about 3 to 6 hours. The product is recovered using conventional techniques, e.g. filtration.

The compounds of formula (II) are prepared according to the following reaction scheme:

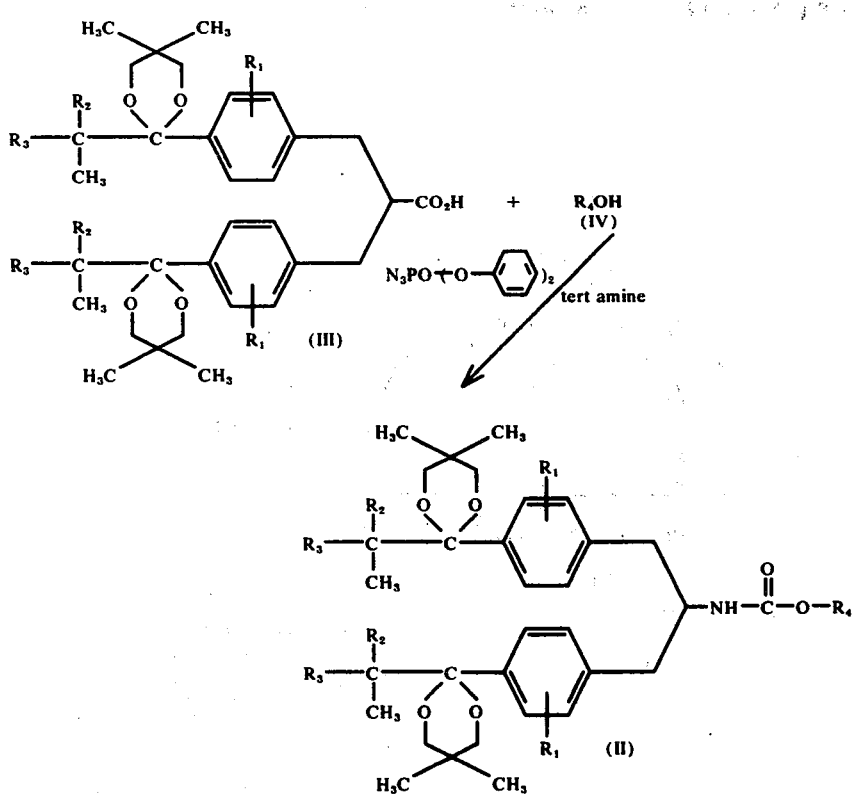

where

R₁, R₂, R₃ and R₄ are as defined above.

The compounds of formula (II) are prepared by reacting a compound of the formula (III) with a compound of the formula (IV) in the presence of diphenylphosphonyl azide and a tertiary amine. The particularly tertiary amine employed is not critical, but it is preferred that the reaction be run in the presence of triethylamine, N,N-diisopropyl ethylamine, and the like, preferably triethylamine. It is to be noted that the compound of formula (IV) is both a reactant and a solvent, and it is therefore critical that an excess of the compound of formula (IV) be utilized, in order that it may also serve as a solvent. The temperature of the reaction is not critical but it is preferred that the reaction be run at a temperature from about 70° to 150° C., preferably the reflux temperature of the solvent. The reaction is run from about 2 to 10 hours, preferably from about 3 to 5 hours. The product is recovered using conventional techniques, e.g. trituration followed by filtration.

The compounds of formula (III) are prepared according to the following reaction scheme:

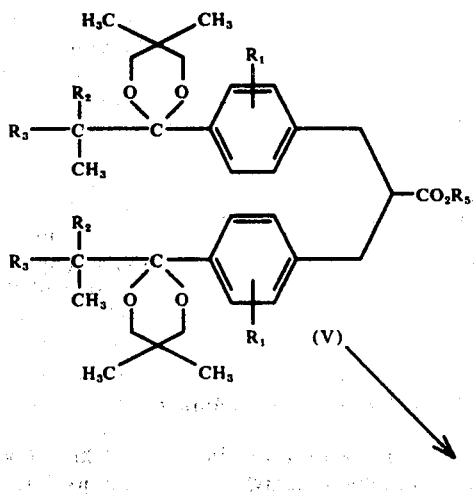

-continued

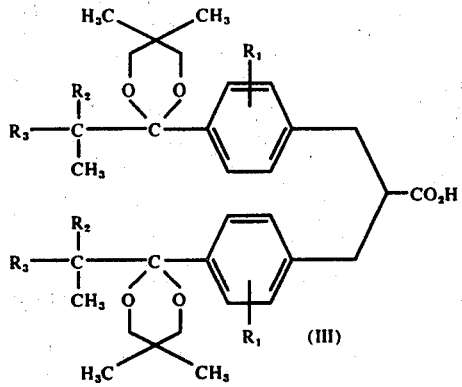

(III)

where $R_5$ represents lower alkyl having 1 to 4 carbon atoms, e.g. methyl, ethyl, isopropyl and the like, and $R_1$, $R_2$ and $R_3$ are as defined above.

The compounds of formula (III) are prepared by hydrolyzing a compound of the formula (IV) with a strong base such as an alkali metal hydroxide, e.g. potassium hydroxide, sodium hydroxide and the like, preferably sodium hydroxide in an aqueous solvent. Although the particular aqueous solvent employed is not critical, it is preferred that the reaction be carried out in water or a mixture of water and a water soluble organic solvent, such as water and a lower alkanol, e.g. water and methanol, water and ethanol and the like, preferably a mixture of water and ethanol. The temperature of the reaction is not critical, but it is preferred that the reaction be run from about 70° to 180° C., preferably the reflux temperature of the solvent. The reaction is run from about 12 to 30 hours, preferably from about 18 to 22 hours. The product is recovered using conventional techniques, e.g. crystallization.

The compounds of formula (V) are prepared according to the following reaction scheme:

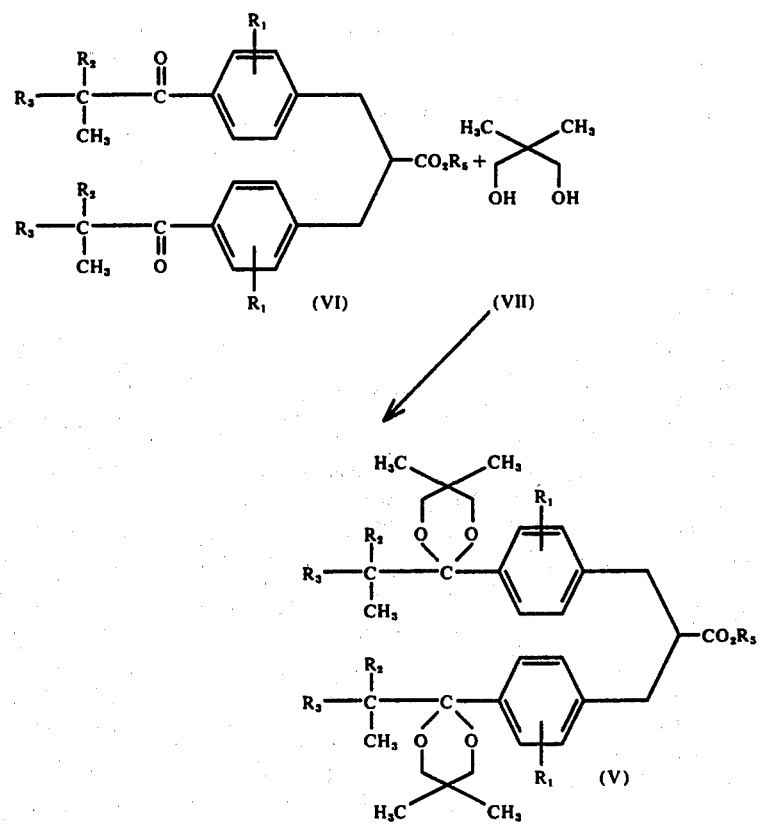

where $R_1$, $R_2$, $R_3$ and $R_5$ are as defined above.

The compound of formula (V) are prepared by reacting a compound of the formula (VI) with a compound of the formula (VII) in the presence of an acid catalyst such as hydrochloric acid, sulfuric acid, polyphosphoric acid or p-toluenesulfonic acid, the latter being especially preferred and in the presence of an inert organic solvent. It is preferred that the reaction be carried out in the presence of an aromatic hydrocarbon such as benzene, toluene and the like, tetrahydrofuran, diethylether or dioxane, preferably toluene. The temperature of the reaction is not critical, but it is preferred that the reaction be run from about 80° to 180° C., preferably the reflux temperature of the solvent.

The reaction is run from about 12 to 30 hours, preferably from about 16 to 20 hours. The product is recovered using conventional techniques, e.g. trituration followed by filtration.

Another aspect of this invention concerns the preparation of the compounds of formula (VI) according to the following reaction scheme:

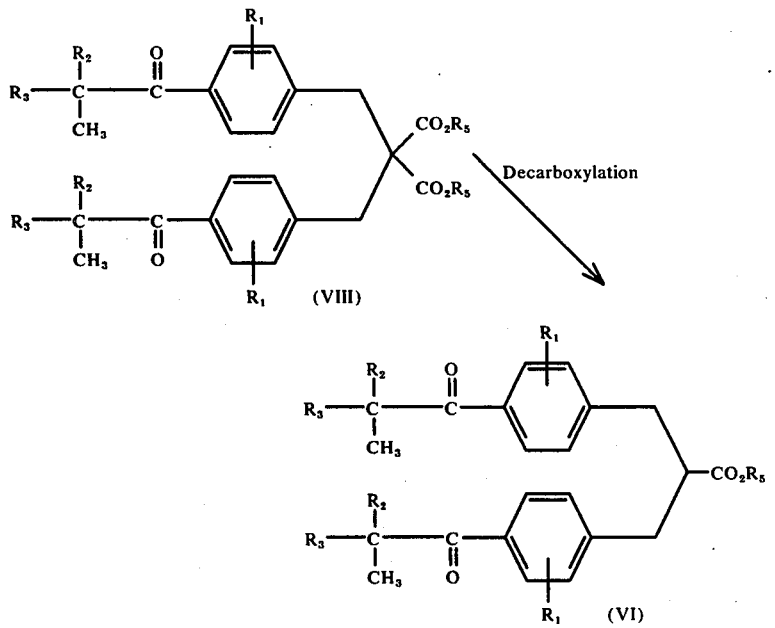

where
R$_1$, R$_2$, R$_3$ and R$_5$ are as defined above.

The compounds of formula (VI) are prepared by decarboxylating a compound of the formula (VIII) in the presence of an alkali metal halide and an inert organic solvent. Although the particular alkali metal halide employed is not critical, it is preferred that the reaction be run in the presence of sodium chloride, potassium chloride, sodium iodide, lithium chloride and the like, preferably sodium chloride. The particular solvent employed is also not critical, but it is preferred that the reaction be carried out in the presence of dimethylacetamide, dimethylformamide, dimethylsulfoxide, tetrahydrofuran or dioxane, preferably dimethylsulfoxide. The temperature of the reaction is not critical, but it is preferred that the reaction be run from about 140° to 220° C., preferably from about 160° to 190° C. The reaction is run from about 12 to 30 hours, preferably from about 20 to 24 hours. The product is recovered using conventional techniques, e.g. crystallization.

Many of the compounds of formulae (IV), (VII), and (VIII) are known and may be prepared by methods described in the literature. The compounds of formula (IV), (VII), and (VIII) not specifically described may be prepared by analogous methods from known starting materials.

The compounds of formula (I) may also exist as acid addition salts, and are readily prepared by reacting the base with an appropriate acid by conventional techniques.

The compounds of formula (I) are useful because they possess pharmacological activity in animals as hypolipidemic agents, as indicated by the fall in cholesterol and triglyceride levels in male albino Wistar rats weighing 110–130 g. initially. The rats are maintained on drug-free laboratory chow diet for seven days and then divided into groups of 8 to 10 animals. Each group with the exception of the control is then given orally 15 to 30 milligrams per kilogram of body weight per diem of the compound for six days. At the end of this period, the animals are anethetized with sodium hexobarbital and bled from the carotid arteries. Serum or plasma samples are collected, and 1.0 ml. samples of the serum are added to 9.0 ml. redistilled isopropanol. Two autoanalyzer cupsful of a mixture of zeolite-copper hydroxide and Lloydds reagent (Kessler, G., and Lederer, H., 1965, Technicon Symposium, Mediad Inc., New York, 345–347) are added, and the mixture is shaken for one hour. Cholesterol and triglyceride levels are determined simultaneously on the same sample by Technicon N 24 A (cholesterol) and N-78 (triglyceride) methodology. The mean total serum cholesterol levels are then computed and the hypocholesterolemic activity is expressed as the fall in cholesterol levels as a percentage of the control level. The change in serum triglyceride levels induced by the drug is computed as a percentage of the control triglyceride levels.

For such usage, the compounds (I) may be combined with a pharmaceutically acceptable carrier or adjuvant and may be administered orally or parenterally as such or admixed with conventional pharmaceutical carriers. They may be administered in such forms as tablets, dispersible powders, granules, capsules, syrups, and elixirs and parenterally as solutions, suspensions, dispersions, emulsions and the like, e.g., a sterile injectable aqueous solution. The dosage will vary depending upon the mode of administration utilized and the particular compound employed.

The compounds of formula (I) may be similarly administered in the form of their non-toxic pharmaceutically acceptable salts. Such salts possess the same order of activity as the free base and are readily prepared by reacting the base with an appropriate acid by conventional techniques and, accordingly, are included within the scope of this invention. Representative of such salts are the mineral acid salts, e.g., hydrochloride, hydrobromide, sulfate and the like, and the organic acid salts such as succinate, benzoate, maleate and the like.

The hypolipidemic effective dosage of compounds (I) employed in the alleviation of lipidemia may vary depending on the particular compound employed and the severity of the condition being treated. However, in general, satisfactory results are obtained when the compounds of formula (I) are administered at a daily dosage of from about 3.0 milligrams to about 250 milligrams per kilogram of animal body weight, preferably given in divided doses two to four times a day, or in sustained release form. For most large mammals, the total daily dosage is from about 200 milligrams to about 1500 milligrams. Dosage forms suitable for internal use comprise from about 50 to about 750 milligrams of the active compound in intimate admixture with a solid or liquid pharmaceutically acceptable carrier or diluent.

A representative deformulation suitable for oral administration 2 to 4 times a day for the treatment of lipidemia is a capsule prepared by standard encapsulating techniques which contains the following:

| Ingredient | Weight (mg) |
| --- | --- |
| 1-bis(p-pivaloylbenzyl) methanamine | 150 |
| inert solid diluent (starch, lactose, kaolin) | 300 |

EXAMPLE 1 bis(p-pivaloylbenzyl)acetic acid ethyl ester

A mixture of 50.0 g. (0.100 mole) bis(p-pivaloylbenzyl)malonic acid diethylester, 6.0 g. (0.103 mole) sodium chloride, 200 ml. dimethylsulfoxide and 3.5 ml. water is heated at 180° for 22 hours. The resulting mixture is then cooled and poured into water. The water mixture is extracted twice with methylene chloride and the methylene chloride washed with water and dried over anhydrous magnesium sulfate, filtered and evaporated in vacuo. The resulting oil is crystallized from pentane to give bis(p-pivaloylbenzyl) acetic acid ethyl ester; m.p. 60°-63° C.

Following the above procedure and using in place of bis(p-pivaloylbenzyl)malonic acid diethyl ester an equivalent amount of
a. bis(2-chloro-4-pivaloylbenzyl)malonic acid diethyl ester, or
b. bis(2-fluoro-4-pivaloylbenzyl)malonic acid diethyl ester, there is obtained
a. bis(2-chloro-4-pivaloylbenzyl)acetic acid ethyl ester, or
b. bis(2-fluoro-4-pivaloylbenzyl)acetic acid ethyl ester, respectively.

EXAMPLE 2 bis(2,2-dimethyl-1,3-propanediyl cyclic acetal)-bis(p-pivaloylbenzyl)acetic acid ethyl ester A mixture of 23.1 g. (0.053 mole) bis(p-pivaloylbenzyl)acetic acid ethyl ester, 16.6 g. (0.159 mole) 2,2-dimethyl-1,3-propanediol, and 0.3 g. p-toluenesulfonic acid in 300 ml. toluene is refluxed, under a water separator, for 18 hours. The mixture is then cooled and the solvent removed in vacuo. The resulting solid is triturated in water/ether, filtered and washed with ether to give bis(2,2-dimethyl-1,3-propanediyl cyclic acetal)-bis(p-pivaloylbenzyl) acetic acid ethyl ester; m.p. 176°-177.5° C.

Following the above procedure and using in place of bis(p-pivaloylbenzyl)acetic acid ethyl ester an equivalent amount of
a. bis(2-chloro-4-pivaloylbenzyl)acetic acid ethyl ester, or
b. bis(2-fluoro-4-pivaloylbenzyl)acetic acid ethyl ster, there is obtained
a. bis(2,3-dimethyl-1,3-propanediyl cyclic acetal)-bis(2-chloro-4-pivaloylbenzyl)acetic acid ethyl acid,t-butyl
b. bis(2,2-dimethyl-1,3-propanediyl cyclic acetal)-bis(2-fluoro-4-pivaloylbenzyl)acetic acid ethyl ester, respectively.

EXAMPLE 3 bis(2,2-dimethyl-1,3-propanediyl cyclic acetal)-bis-(p-pivaloylbenzyl)acetic acid A mixture of 13.1 g. (0.022 mole) bis(2,2-dimethyl-1,3-propandeiyl cyclic acetal)-bis(p-pivaloylbenzyl)acetic acid ethyl ester in 130 ml. ethanol is treated with 13.0 g. (0.325 mole) sodium hydroxide in 50 ml. water and the resulting mixture refluxed for 20 hours. The mixture is cooled and the ethanol removed in vacuo. The resulting mixture is cooled and made acidic by the addition of 2N hydrochloric acid. The acidic mixture is extracted twice with methylene chloride, the organic solution dried over anhydrous magnesium sulfate, filtered and the solvent removed in vacuo. The resulting foam is crystallized from heptane to give bis(2,2-dimethyl-1,3-propanediyl cyclic acetal)-bis(p-pivaloylbenzyl) acetic acid; m.p. 175°-176° C.

Following the above procedure and using in place of bis(2,2-dimethyl-1,3-propanediyl cyclic acetal)-bis(p-pivaloylbenzyl)acetic acid ethyl ester, an equivalent amount of
a. bis(2,2-dimethyl-1,3-propanediyl cyclic acetal)-bis(2-chloro-4-pivaloylbenzyl)acetic acid ethyl ester, or
b. bis(2,2-dimethyl-1,3-propanediyl cyclic acetal)-bis(12-fluoro-4-pivaloylbenzyl)acetic acid ethyl ester, there is obtained
a. bis(2,2-dimethyl-1,3-propanediyl cyclic acetal)-bis(2-chloro-4-pivaloylbenzyl)acetic acid, or
b. bis(2,2-dimethyl-1,3-propanediyl cyclic acetal)-bis(2-fluoro-4-pivaloylbenzyl)acetic acid, respectively.

EXAMPLE 4 bis(2,2-dimethyl-1,3-propanediyl cyclic acetal)-N-[bis(p-pivaloylbenzyl)methyl]carbamic acid,t-butyl ester A mixture of 7.4 g. (0.0127 mole) bis(2,2-dimethyl-1,3-propanediyl cyclic acetal)-bis(p-pivaloylbenzyl)acetic acid, 3.5 g. (0.0127 mole) diphenylphosphonylazide, 1.3 g. (0.0127 mole) triethylamine and 9.9 g. (0.134 mole) t-butanol is heated to reflux for 4 hours. The mixture is cooled and the excess t-butanol removed in vacuo. The resulting solid is washed with ether, 2N hydrochloric acid, 2N sodium hydroxide and then water, dried in vacuo to give bis(2,2-dimethyl-1,3-propanediyl cyclic acetal)-N-[bis(p-pivaloylbenzyl)-methyl]carbamic acid,t-butyl ester; m.p. 151°-153.5° C.

Following the above procedure and using in place of bis(2,2-dimethyl-1,3-propanediyl cyclic acetal)-bis(p-pivaloylbenzyl)acetic acid, an equivalent amount of a. bis(2,2-dimethyl-1,3-propanediyl cyclic acetal)-bis(2-chloro-4-pivaloylbenzyl)acetic acid, or b. bis(2,2-dimethyl-1,3-propanediyl cyclic acetal)-bis(2-fluoro-4-pivaloylbenzyl)acetic acid, there is obtained a. bis(2,2-dimethyl-1,3-propanediyl cyclic acetal)-N-[bis(2-chloro-4-pivaloylbenzyl)methyl]carbamic acid,t-butyl ester, or b. bis(2,2-dimethyl-1,3-propanediyl cyclic acetal)-N-[bis(2-fluoro-4-pivaloylbenzyl)methyl]carbamic acid,t-butyl ester, respectively.

Again following the above procedure and using in place of t-butanol an equivalent amount of methanol there is obtained c. bis(2,2-dimethyl-1,3-propanediyl cyclic acetal)-N-[bis(4-pivaloylbenzyl)methyl]carbamic acid, methyl ester.

EXAMPLE 5

1-bis(p-pivaloylbenzyl)methanamine

A mixture of 5.6 g. (0.00860 mole) bis(2,2-dimethyl-1,3-propanediyl cyclic acetal)-N-[bis(p-pivaloylbenzyl)methyl]carbamic acid,t-butyl ester and 100 ml. concentrated hydrochloric acid is refluxed for 4.5 hours, the mixture is then cooled and filtered and the solid washed thoroughly with water and then with ether, dried in vacuo to give 1-bis(p-pivaloylbenzyl)methanamine hydrochloride; m.p. 267°–268° C.

Following the above procedure and using in place of bis(2,2-dimethyl-1,3-propanediyl cyclic acetal)-N-[bis(p-pivaloylbenzyl)methyl]carbamic acid,t-butyl ester, an equivalent amount of a. bis(2,2-dimethyl-1,3-propanediyl cyclic acetal)-N-[bis(2-chloro-4-pivaloylbenzyl)methyl]carbamic acid, t-butyl ester, or b. bis(2,2-dimethyl-1,3-propanediyl cyclic acetal-N-[bis(2-fluoro-4-pivaloylbenzyl)methyl]carbamic acid,t-butyl ester, there is obtained a. 1-bis(2-chloro-4-pivaloylbenzyl)methanamine hydrochloride, or b. 1-bis(2-fluoro-4-pivaloylbenzyl)methanamine hydrochloride, respectively.

The 1-bis(p-pivaloylbenzyl)methanamine of this example is an effective hypolipidemic agent when orally administered to an animal suffering from lipidemia at a dosge of 150 mg. four times per day.

What is claimed is:

1. A compound of the formula

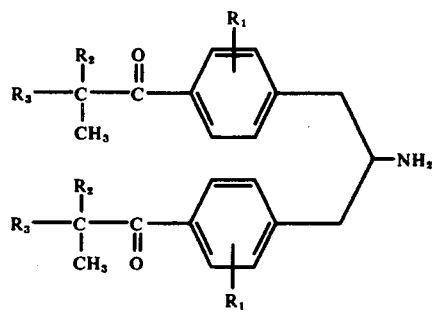

where $R_1$ represents hydrogen, halo having an atomic weight of about 19 to 36, and $R_2$ and $R_3$ each independently represent lower alkyl having 1 to 2 carbon atoms, or a pharmaceutically acceptable acid addition salt thereof.

2. A compound of the formula

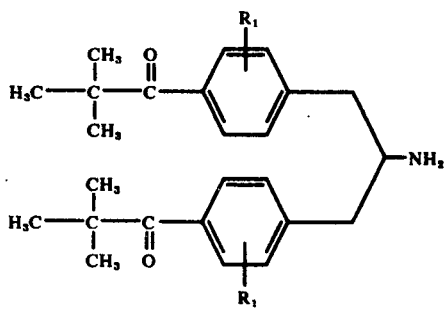

where $R_1$ is as defined in claim 1, or a pharmaceutically acceptable acid addition salt thereof.

3. The compound of claim 2 which is 1-bis(p-pivaloylbenzyl)methanamine hydrochloride.

4. The compound of claim 2 which is 1-bis(p-pivaloylbenzyl)methanamine.

5. A pharmaceutical composition for use in the treatment of lipidemia comprising an effective amount of a compound of claim 1 and a pharmaceutically acceptable diluent or carrier therefor.

6. A method of treating lipidemia which comprises administering to a mammal in need of said treatment a hypolipidemic effective amount of a compound of claim 1.

* * * * *